United States Patent [19]

Taubman et al.

[11] 4,250,262
[45] Feb. 10, 1981

[54] METHOD OF PREPARING A PURIFIED GLUCOSYLTRANSFERASE

[75] Inventors: Martin A. Taubman, Newton; Daniel J. Smith, Natick, both of Mass.

[73] Assignee: Forsyth Dental Infirmary for Children, Boston, Mass.

[21] Appl. No.: 103,590

[22] Filed: Dec. 14, 1979

Related U.S. Application Data

[60] Continuation of Ser. No. 956,847, Nov. 2, 1978, abandoned, which is a division of Ser. No. 879,432, Feb. 21, 1978, Pat. No. 4,150,116.

[51] Int. Cl.³ .................................................. C12N 9/10
[52] U.S. Cl. .................................... 435/193; 435/815; 435/885
[58] Field of Search .......................................... 435/193

[56] References Cited

U.S. PATENT DOCUMENTS 3,993,747  11/1976  Gaffar et al. ............................ 424/88

OTHER PUBLICATIONS

Taubman et al., The Journal of Immunology, vol. 118, No. 2, pp. 710–720 (Feb. 1977).
Guggenheim et al., Dental Plaque, pp. 287–296 (1970) McHugh ed., Dundee, Scotland.

*Primary Examiner*—Lionel M. Shapiro
*Attorney, Agent, or Firm*—Richard P. Crowley

[57] ABSTRACT

Immunization of animals with preparations containing more purified forms of glucosyltransferase (GTF) results in the presence of antibody in saliva demonstrable by functional inhibitions of enzyme activity and binding of radioactive enzyme. Serum antibody was also present. Immunized groups of animals had lower mean caries scores than comparably sham-immunized or nonimmunized control groups. Local immunization with GTF of serotype c or g of a *Streptococcus mutans* reduces the colonization, caries, and lesions caused by infection with *S. mutans* of serotype g (strain 6715) or c, or with serotype g or c, or with serotype a or g, respectively.

13 Claims, No Drawings

METHOD OF PREPARING A PURIFIED GLUCOSYLTRANSFERASE

BASIS OF WORK

The invention described and claimed in this application has been developed, in whole or in part, under NIDR Grant No. DE-000 24, DE-04733 and DE-70122 and Contract No. DE-42438 of the National Institute of Health, Department of Health, Education and Welfare.

This is a continuation of application Ser. No. 956,847, filed Nov. 2, 1978, now abandoned (which application is a division of Ser. No. 879,432, filed Feb. 21, 1978 (now U.S. Pat. No. 4,150,116, issued Apr. 17, 1979).

BACKGROUND OF THE INVENTION (1) Field of the Invention

This invention relates to the prevention of dental caries, and more particularly to the immunization against caries employing the glucosyl transferase (dextransucrase) enzyme (GTF) involved in the synthesis of the water-insoluble extracellular polysaccharide from sucrose by the action of cariogenic bacteria. More specifically, it relates to methods of obtaining more highly purified glucosyl transferase enzyme. It further relates to cross protection via immunization with serotype c GTF, or with serotype g CTF or with serotype a GTF.

(2) Description of the Prior Art

Dental caries is the most prevalent infectious disease in the western world, and the cost of its treatment exceeds that of any single bacterial infection.

Studies have indicated that the formation of carious lesions on teeth is related to the interaction between carbohydrates (notably sucrose) in the diet and specific bacteria on tooth surfaces. The cariogenic bacteria, predominantly streptococci, adhere to the surfaces of teeth by synthesizing extracellular polysaccharides from sucrose. *Streptococcus mutans* is the principle organism associated with dental caries in humans and will also produce disease in rodents and in primate models. O'Brian, T. C. 1976. Introduction and rationale for continued investigations on a vaccine as an approach to dental caries prevention. *Immunology Abstracts* (Special issue): 3. Gibbons, R. J. and J. van Houte. 1975. Bacterial adherence in oral microbial ecology, *Ann. Rev. Microbiol.* 29:19. These organisms ferment carbohydrate moieties which results in the production of acid leading to demineralization of the tooth enamel.

These polysaccharides, which are generally either polyglucans or polyfructans (levan), "glue" the bacterial cells together and help them adhere to the teeth. Two polysaccharides thus promote action between the bacteria and further sucrose ingested by the Host animal and thereby facilitate the formation of further polysaccharides. Moreover, the extracellular polysaccharides thus produced are believed to play significant roles in plaque formation and in the consequent development of caries. The polysaccharide polymers are synthesized from sucrose by a group of extracellular and cell-associated consitutive enzymes collectively called glucosyltransferase (GTF).

At least two types of GTF enzymes have been described on the basis of the product synthesized. One type of GTF enzyme(s) will synthesize predominantly water-insoluble glucose polymers (called mutan). Guggenheim, B. 1970. Enzymatic hydrolysis and structure of water-insoluble glucan produced by glucosyltransferases from a strain of *Streptococcus mutans. Helv. Odontol.* Acta 14:89. A second type of GTF enzyme(s) is primarily responsible for the synthesis of water-soluble glucose polymers, which consist predominantly of al-6 linkages. Mutan, containing significant additional al-3 linkages appears to be important in the adherence phenomena of *S. mutans.* Mukasa, H., and H. D. Slade. 1973. Mechanisms of adherence of *S. mutans* to smooth surfaces. I. Roles of insoluble dextran-levan synthetase enzymes and cell wall polysaccharide antigens in plaque formation. *Infect. Immun.* 8:555.

*S. mutans* cells have been used in experiments designed to study the effects of immunization on experimental dental caries in rodent and primate model systems. Taubman, M. A. 1973. Role of immunization in dental disease. In Comparative Immunology of the Oral Cavity. Edited by S. Mergenhagen and H. Scherp. U.S. Government Printing Office, Washington, D.C. P. 138. Taubman, M. A., and D. J. Smith, 1974. Effects of local immunization with *Streptococcus mutans* on induction of salivary IgA antibody and experimental dental caries in rats. *Infect. Immun.* 9:1079. McGhee, J. R., S. M. Michalek, J. Webb, J. M. Navia, A. F. R. Rahman, and D. W. Legler. 1975. Effective immunity to dental caries: protection of gnotobiotic rats of local immunization with *Streptococcus mutans. J. Immunol.* 114:300. Bowen, W. H., B. Cohen, M. F. Cole, and G. Colman. 1975. Immunization against dental caries. *British Dent. J.* 139:45. Lehner, T., S. J. Challacombe, and J. Caldwell. 1975. Immunological and bacteriological basis for vaccination against dental caries in Rhesus monkeys. *Nature* 254:517. Evans, R. T., F. G. Emmings, and R. J. Genco. 1975. Prevention of *Streptococcus mutans* infection of tooth surfaces by salivary antibody in irus monkeys; (*Macaca fasicularis*). *Infect. Immun.* 12:293. In these experiments the use of whole cell antigens, which often bear GTF on the surface, has resulted in diminished colonization of S. mutans or reduced dental caries formation. Immunized animals often contained demonstrable serum and/or salivary antibody to GTF in addition to antibody of other specificities. Emmings, F. G., R. T. Evans; and R. J. Genco. 1975. Antibody response in the parotid fluid and serum of irus monkeys (*Macaca fasicularis*) after local immunization with *Streptococcus mutans. Infect. Immun.* 12:281; Russell, M. W., S. J. Challacombe, and T. Lehner. 1976. Serum glucosyltransferase-inhibiting antibodies and dental caries in Rhesus monkeys immunized against *Streptococcus mutans. Immunology* 30:619; Genco, R. J., R. T. Evans, and M. A. Taubman. 1974. Specificity of antibodies to *Streptococcus mutans;* significance in inhibition of adherence. *Adv. Exp. Med. Biol.* 45:327.

The use of materials containing GRF enzymatic activity as antigens has, at times, also resulted in caries reductions in preliminary experiments using the rodent model. Hayashi, J. A., I. L. Shklair, and A. N. Bahn. 1972. Immunization with dextransucrases and glycosidic hydrolases. *J. Dent. Res.* 51:436. However, similar experiments in primates have seldem shown reductions. Lehner, T., S. J. Challacombe, and J. Caldwell. 1975. An immunological investigation into the prevention of caries in deciduous teeth of Rhesus monkeys. Arch. Oral Biol. 20:305.

*In vitro* experiments have demonstrated that antibody to GTF can interfere with the formation of the polysaccharide product as well as reduce the adherence of *S. mutans* to hard surfaces such as wire or glass. Fukui, K. Y. Fukui, and T. Moriyama. 1974. Some immunochemical properties of dextransucrase and invertase from *Streptococcus mutans. Infect. Immun.* 10:985. Therefore, the significance of GTF in the manifestation of *S. mutans* virulence, the ability to immunologically inhibit GTF enzyme function, and the presence of antibody directed to GTF in animals protected against caries, implicated these enzymes as potential antigens for the study of the effects of immunization on experimental dental caries.

A number of vaccines have been proposed for immunization against dental caries in animals. Various of these proposals are summarized in U.S. Pat. No. 3,879,545. The invention claimed in that patent relates to caries-preventive vaccines incorporating as the active ingredient thereof a polyfructan (or levan) polysaccharide produced by elaboration of certain strains of streptococcus, particularly *Streptococcus* Strain *SS2*. The immunization technique, according to the patentee, has been found to result in the formation of antibodies against the heterogeneous micro-organisms in the recticuloendothelial system and in the blood, and to result in significant decreases in the formation of carious lesions in host animals subjected to innoculation with such organisms. However, the patentees also disclose investigating the use of dextransucrase enzyme for immunization against caries formation.

As disclosed in U.S. Pat. No. 3,879,545, the patentees had believed that since the enzymes dextransucrase and levansucrase are produced by *S. mutans* and *S.* Strain *SS2*, respectively, and are involved in the synthesis of dextran and levan, and these polysaccharides are believed to produce caries, that immunization with these enzymes might result in the production of antibodies to the enzymes which would neutralize their activity in vivo, thus inhibiting synthesis of the polysaccharides and resulting in decreased plaque formations and lowered incidence of caries. The patentees disclose, however, that their experimentations failed to confirm this hypothesis. Nevertheless, the data disclosed did appear to show that while enzyme preparations purified as described by Guggenheim and Newbrun in Helv. *Odontol. Acta.* 13:84-97 (1969) were ineffective in two routes of systemic immunization, a more crude form was somewhat effective against infectious inoculations with *S. mutans* 6715.

In U.S. Pat. No. 3,931,398 there is disclosed a locally administered vaccine containing dextransucrase (glucosyl transferase). As disclosed in the patent, this somewhat impure enzyme was prepared by the method of Guggenheim and Newbrun, supra, from the supernatant liquid of an 18-hour culture of *S. mutans* 6715 grown on 8% sucrose. These preparations, as disclosed in the patent, had 10 units of dextransucrase activity per mg. of protein, one unit of the enzyme being defined as the amount required to catalyze transformation of 1 mg. of sucrose to dextran in 1 hour (releasing 0.52 mg. of fructose) at pH 6.8. The activity was measured by determining the amount of released reducing sugars. While the patentee speculates that the use of purer forms of the dextransucrase enzyme would result in further diminution of the mean caries scores disclosed, no method is disclosed in this patent of obtaining a purer form of the enzyme.

SUMMARY OF THE INVENTION

In accordance with one aspect of the present invention, the invention is based upon certain methods for recovering the enzyme glucosyl transferase from *Streptococcus mutans* in various stages of purification, and to the use of these purer forms of the enzyme in local immunization against dental caries.

The first method of purifying GTF involves the further purifications by gel filtration of the somewhat impure, purified GTF obtained by the methods of Guggenheim, B., and E. Newbrun. 1969. Extracellular glucosyltransferase activity of HS strain of *Streptococcus mutans. Helv. Odontol. Acta* 13:84, and which is disclosed in U.S. Pat. No. 3,931,398.

A second method of purification according to the invention involves an enzyme antigen preparation obtained by chromatography of dialyzed, concentrated *S. mutans* culture supernatants on diethylaminoethyl (DEAE)—cellulose, followed by gel filtration.

Defined enzyme antigens (DE-1 and DE-2) were prepared in a third method of purification from concentrated *S. mutans* culture supernatant by DEAE-cellulose chromatography followed by gel filtrations, these being the two GTF fractions obtained after filtration. These are used accordance with the invention as separate antigens.

In the synthesis of mutan, a portion of GTF-remains non-covalently bound to the polysaccharide. A further method of obtaining more purified GTF according to the invention involves the recovery of the GTF from the polysaccharide by use of a denaturing solvent. This method differs quite distinctly from the other methods of the invention, and from the prior art of which we are aware in that the enzyme is recovered from the polysaccharide product, rather than from the culture supernatant.

Quite advantageously, in accordance with a further aspect of the invention, it has been discovered that
 (1) Glucosyltransferase serotypes a and g are closely related antigenically but are more distantly related to GTF of serotype c, based on assays of inhibition of total glucan synthesis,
 (2) Local immunization with GTF from serotype c or serotype g or serotype a *S. mutans* reduces the colonization, caries, and lesions caused by infection with the respective homologous strain compared with sham-injected controls; and
 (3) Local immunization with GTF of serotype c or serotype g or serotype a *S. mutans* reduces the colonization, caries, and lesions caused by infection with heterologous *S. mutans* of serotype g (strain 6715), or serotype c (Ingbritt) or serotype g (6715), respectively.

DETAILED DESCRIPTION OF THE INVENTION AND THE PREFERRED EMBODIMENTS

EXAMPLE 1

GROWTH OF CULTURE MEDIUM AND CRUDE ANTIGEN PREPARATION

*Streptococcus mutans* strain 6715, a cariogenic bacteria in rats and hamsters, originally isolated from humans and resistant to streptomycin at concentrations of 2000 $\mu$g/ml. was grown anaerobically (10% $CO_2$, 90% $N_2$) for 18 to 36 hr at 37° C. in 6 to 10 liters of dialyzate of Brain Heart Infusion medium (BHI) available commercially from Baltimore Biological Laboratories (BBL). This dialyzable medium had been supplemented with 0.8% glucose and 3 g/liter of $K_2HOPO_4$, Carlsson, J., E. Newbrun, and B. K. Krasse. 1969. Purification and properties of dextransucrase from *Streptococcus*

*sanguis. Arch. Oral Biol.* 14:469. Glucosegrown cells were used since these conditions maximize the amount of GTF in the culture supernatant, Spinell, D. M., and R. J. Gibbons. 1975. Influence of culture medium on the glucosyltransferase and dextran binding capacity of *Streptococcus mutans* 6715 cells. *Infect. Immun.* 10:1448. After removal of the cells by centriguration (18,000×G) the culture supernatant was concentrated by negative pressure at 4° C.

EXAMPLE 2

PURIFICATION OF GTF BY GEL FILTRATION

The concentrated culture supernatant in Example 1 was subjected to hydroxylapatite chromatography after the technique of Guggenheim and Newbrun, supra, to obtain a somewhat impure dextransucrase (GTF). Enzymatic activity which formed waterinsoluble polysaccharide was then filtered on a column of Sepharose 4B. One peak of GTF activity was observed to elute with a relative elution volume (REV=$V_e/V_O$, where $V_e$=elution volume and $V_O$=void volume) of 2.1 and formed a cloudy, fine product upon incubation with 0.125 M sucrose for 4 hr. Glucose accounted for less than 20% of the total reducing sugar released during polysaccharide synthesis as determined by the Somogyi (Somogyi, M. 1945. A new reagent for the determination of sugars. *J. Biol. Chem.* 160:61) and Glucostat (Worthington Biochemical Corp., Freehold, N. J.) assays. The enzyme-containing fraction (antigen No. 1-CE-1) was shown as hereafter disclosed to contain at least three antigens, one of which was enzyme when tested in gel diffusion and immunoelectrophoretic analysis against a rabbit antiserum to the antigen. No serotype-specific carbohydrate antigen was detected, either in this preparation with purified antibody directed to the *S. mutans* 6715 antigen, (Iacono, V. J., M. A. Taubman, D. J. Smith, and E. C. Moreno. 1976. A spectro-photometric procedure for quantitation of antibody directed to bacterial antigens. *Immunochemistry* 13:235), or in any of the following enzyme preparations directed in Examples 3 and 4. In addition, the serums of rats and hamsters immunized with these antigen preparations did not react with purified serotype-specific carbohydrate antigen of *S. mutans* 6715, Iacono, V. J., M. A. Taubman, D. J. Smith, and M. J. Levine. 1975. Isolation and immunochemical characterization of the group-specific antigen of *Streptococcus mutans* 6715. *Infect. Immun.* 11:117.

EXAMPLE 3

PURIFICATION OF GTF BY DEAE-CELLULOSE CHROMATOGRAPHY AND GEL FILTRATION

Preparations were obtained by chromatography of dialyzed, concentrated S. mutans culture supernatants according to Example 1 on diethylaminoethyl (DEAE)-cellulose in accordance with usual techniques. All water-insoluble polysaccharide-forming enzymatic activity was then eluted by stepwise addition of 0.2 M NaCl and 0.5 M NaCl in 0.01 M phosphate buffer (PB) pH 6.8, or with a gradient to 0.5 M NaCl in PB. This activity was then conventionally filtered on a column of Sepharose 4B. All fractions free of serotype antigen which synthesized polysaccharide when incubated with 0.125 M sucrose were combined and referred to as Antigen No. 2 (CE-2). This material included that which eluted at the void volume (REV=1) and that which eluted later in the profile (REV=2).

The percentage of glucose released during polysaccharide synthesis when the antigen was incubated with sucrose was similar to that of Antigen No. 1. Gel diffusion analyses of Antigen No. 2 against the serums of conventional rats immunized with either antigen showed at least two or three components. At least one identical component and often two were detected by these serums and the serums of gnotobiotic rats (G) immunized with Antigen No. 2 or hamsters (H) immunized with DE-1 or DE-2 as later more fully disclosed. The G serums detected at least four or five components in gel diffusion analysis and the H serums at least three or at least five components, respectively. Enzyme to be used for the gnotobiotic rat experiment was filter-sterilized.

EXAMPLE 4

TWO GTF FRACTIONS OBTAINED FOR USE AS SEPARATE ANTIGENS

Defined enzyme antigens were prepared from concentrated *S. mutans* culture supernatant by DEAE-cellulose chromatography followed by Sepharose 4B gel filtration techniques also used in the preparation of Antigen No. 2. However, after gel filtration two GTF fractions (DE-1 and DE-2) were obtained for use as separate antigens. De-1 eluted at the void volume and synthesized a flocculant water-insoluble product upon incubation with sucrose. Fructose was the principal sugar released (76%). This amount of glucose release (24%) can be directly attributed to GTF enzymatic activity of *S. mutans* strain 6715. Ciardi, J. E., G. J. Hageage, Jr., and C. L. Wittenberger. 1976. Multicomponent nature of the glucosyltransferase system of *Streptococcus mutans.* J. Dent. Res. 55 (Special Issue C):C87. Little polysaccharide was observed after addition of ethanol, to 75%, to the centrifuged supernatant. Polyacrylamide gel electrophoresis on 7% gels in tris (hydroxymethyl) amino-methane-glycine buffer (pH 8.8) was performed. Davis, B. J. 1964. Disc electrophoresis II. Methods and application to human serum proteins. *Ann. N. Y. Acad. Sci.* 121:404. Samples were applied to glycerol directly onto the separating gel surface. After electrophoresis (4 mA/gel) for 45 min the gel was sliced longitudinally; one-half was incubated in 0.125 M sucrose at 37° C. for 16 hr and the other half was stained with Amido-black (5%). It was seen that the one band which entered the gel corresponded to the single band of insoluble polysaccharide formed by the enzyme from sucrose. Protein and GTP activity also remained at the origin.

The second GTF fraction, DE-2, eluted from the Sepharose 4B column with a relative elution volume of 1.9. Although some finely dispersed water-insoluble polysaccharide was synthesized by DE-2, considerable polymerization was observed after addition of ethanol, to 75%, to the centrifuged supernatant. Fructose was the principal sugar released (83%). Many stained bands could be observed after polyacrylamide gel electrophoresis. However, no definite band of water-soluble polysaccharide could be seen in the gels, after 16 hr incubation with sucrose.

DE-1 contained at least one and DE-2 at least three antigenic components identifiable by gel diffusion analyses against rat antiserums to Antigen No. 2. Gel diffusion analyses of the serums of hamsters immunized with DE-1 vs the DE-1 and DE-2 preparations revealed at least two antigenic components in DE-1, at least one of which was immunologically identical to one component of at least four detected in DE-2. Hamster antiserums to DE-2 detected at least three components in Antigen No. 1, at least one of which was immunologically identical to one of at least four components detected in DE-2. After immunoelectrophoresis (IEP) of the DE antigens, at least one component demonstrating the same mobility in each preparation was shown to have enzyme activity after placement of sucrose in the trough. A second enzyme component was seen in DE-1. The maximum number of components seen after IEP with either serum to DE-1 was at least three and, in DE-2, at least eight.

EXAMPLE 5

IMMUNIZATION AND INFECTION

Two immunization experiments (P) were performed in initially pathogen-free rats (CD strain, Charles River), in addition to one experiment (G) in initially germfree rats (Forsyth strain) and one experiment (H) in NIH-white hamsters. Both rat strains were initially derived from Sprague-Dawley rats. The rats and hamsters did not harbor S. Mutans indigenously.

In experiment P1, 38 pathogen-free rats were divided into four groups: (I) nonimmunized and noninfected, (II) nonimmunized and infected, (III) sham-immunized with 0.1 ml phosphate-buffered saline (PBS) incorporated into 0.1 ml of complete Freund's adjuvant (CFA, Difco Laboratories, Detroit, Mich.) and infected; (IV) immunized with 0.1 ml enzyme incorporated into 0.1 ml CFA and infected. In experiment P2, 59 pathogen-free rats were divided into three groups (groups I, III, IV).

Immunization was initiated when the animals were 21 (P1) or 20 (P2) days of age. The animals in groups III and IV were injected subcutaneously at 7- to 12-day-intervals in the vicinity of the parotid and submandibular glands five times before infection. Rats in group IV of experiment P1 were injected with 0.1 mg of Antigen No. 1 which contained 1.8 units of activity (unit=the amount of enzyme converting 1 mg sucrose to glucan in 1 hr. releasing 0.52 mg fructose). Koepsell, H. J., and H. M. Tsuchiya. 1952. Enzymatic synthesis of dextran. *J. Bacteriol.* 63:293. Rats in group IV of P2 were injected with 0.5 mg of Antigen No. 2 which contained 2.0 units of activity. Subsequent injections were given at 20- to 30-day intervals after infection. Weanling rats for these experiments were derived from mothers which had been maintained on a low fluoride low carbohydrate diet L-356 (General Biochemicals, Chagrin Falls, Ohio) throughout pregnancy until weaning. Experimental rats were continued on this diet until the week preceding infection when they were given diet 2000 which was continued until experimental termination. Keyes, P. H., and H. V. Jordan. 1964. Periodontal lesions in the Syrian hamster. III. F lings related to an infectious and transmissible component. Arch. Oral Biol. 9:377

The experiment initiated in germfree (G) rats followed essentially the same protocol as the P experiments. Since dental caries does not occur in germfree conditions only two groups of animals were used, corresponding to groups III and IV. These animals were housed in the same isolator. At 24 days of age the rats in group IV were given a series of three injections of Antigen No. 2 (0.5 mg containing 2 units of activity/rat) incorporated into CFA administered before injection (53 days of age). Rats in group III were injected on the same days with CFA and PBS. Three rats from groups III and IV were removed from the isolator at 53 days for analysis of serum and saliva. Periodic swabbing of the animals in the isolator during the experiment revealed the absence of microorganisms before infection and only S. mutans 6715 after infection. Rats in the G experiment were maintained on cariogenic diet 2000 from weaning until the experiment was terminated.

Hamsters were immunized with the defined enzyme preparations (DE-1 and DE-2). The general treatment of hamsters in groups I and III was identical to the comparable groups in the rat experiments. Immunized hamsters were divided into two groups: (IV A) injected with 0.1 ml of DE-1 (containing 1.6 units of activity) incorporated into 0.1 ml CFA, and (IV B) injected with 0.1 ml of DE-2 (containing 1.6 units of activity incorporated into 0.1 ml CFA. Four injections were given at 7-day-intervals in the salivary gland vicinity (SGV) before infection and one injection was given midway in the 39-day infection period. All hamsters were maintained on Purine Lab Chow, in meal form, from weaning to 3 days before infection when diet 2000 was initiated.

S. mutans strain 6715 organisms were passaged in conventional rats maintained on diet 2000. These organisms were reisolated periodically for purposes of infection. The rats and hamsters in groups II, III and IV were orally infected with 0.4 ml of a 20 hr culture of S. mutans 6715 (approximately $10^8$ colony-forming units, (C.F.U.) 10 to 11 days after completion of the initial immunization regimen. Hamsters were infected on days 52 and 53; P1 rats; Days 74 and 79; P2 rats; Days 68,69, 103, 104, 109 and 110; and G1 rats: Day 53. Before this time salivary (and serum) GTF-inhibiting activity could be demonstrated in all the immunized animals. The flora of all animals was periodically monitored after infection as described previously. Taubman, M. A. and D. J. Smith, 1974. Infect. Immun. 9:1079.

At the termination of the experiment (39 to 119 days after infection) saliva was collected and the animals were exsanguinated. Streptomycin-resistant S. mutans 6715, total organisms, caries and lesions were determined in P1 as previously described. Taubman and Smith, supra. In experiments P2, G1 and H1, bacteriologic data were obtained by removing all bacterial plaque from the buccal and lingual surfaces of the teeth with a number 6 explorer. Plaque was then sonicated for 10 sec at maximum amplitude in 2 ml of ¼ strength Ringer's solution, appropriately diluted and plated on mitis-salivarius (MS) agar and MS agar containing 200 μg streptomycin/ml (MSS). The whole jaws were then defleshed and all caries and lesions were scored by the modified Keyes method, Taubman and Smith, supra, without knowledge of the group designation of the animal.

Differences among means were determined by analysis of variance. Individual means were also compared by analysis of variance. In all experiments comparisons were made between the immunized group IV and the sham-immunized group III or between the untreated control group I and the sham-immunized group III. The results are tabulated below.

Salivas and serums were collected and treated before antibody assay as previously described. Taubman, M. A. and D. J. Smith. 1974. *Infect. Immun.* 9:1079. In addition, saliva to be used in the inhibition of $^{14}C$-glucose incorporation assays was dialyzed, first against PBS containing 0.001 M EDTA, then against 0.01 M phosphate buffer, pH 6.8.

EXAMPLE 6

PREPARATION OF ANTISERUMS

The preparation and monospecificity of rabbit anti-rat secretory IgA serum has been previously described. Taubman, M. A. 1973. U. S. G. P. O., Taubman, M. A. and D. J. Smith, *Infect. Immun.* 9:1079, both supra. Before use the globulins from this serum were precipitated with ammonium sulfate at 33% saturation, washed three times with 40% saturated ammonium sulfate and reconstituted to one-fifth the original serum volume in PBS. Quantitative precipitin analyses with the anti-rat IgA reagent showed that 10 µl was in excess of the amount necessary to react with all the IgA in 140 µl of saliva from normal or from hyperimmunized rats.

The preparation of a rabbit antiserum directed to rat IgG has also been previously described in the immediately preceding noted publication. This antiserum reacted with rat IgG1 and IgG2 and also had light (L) chain reactivity.

Before adsorption, the globulins from this serum were precipitated with ammonium sulfate at 33% saturation, washed three times with 40% saturated ammonium sulfate and reconstituted to the original serum volume in PBS. This anti-rat IgG globulin was treated with an immunoadsorbent prepared by reacting cyanogen bromide-activated Sepharose 6B (Axen, R. J., Porath, and S. E. Ernback. 1967. Chemical coupling of peptides and proteins to polysaccharides by means of cyanogen halides. *Nature* 214:1302.) with a 20 hour pepsin digest (Utsumi, S., and F. Karush. 1965. Peptic fragmentation of rabbit γ G-immunoglobulin *Biochemistry* 4:1766) of DEAE-cellulose purified rat IgG and/or treated with an immunoadsorbent prepared from cyanogen bromide-activated Sepharose 4B and an IgA-rich fraction of rat colostrum (prepared by gel filtration through tandem columns of Sephadex G-200 and Sepharose 6B). Subsequent gel diffusion and immunoelectrophoretic analyses of the adsorbed globulin showed no reactivity with rat secretory IgA or IgM and reactivity with rat IgG. Quantitative precipitin analyses with the pooled monospecific anti-rat IgG globulin showed that 50 µl was in excess of the amount necessary to precipitate all the IgG in 5 µl of hyperimmunized or normal rat serum.

Goat anti-rabbit IgG was prepared as previously described or was purchased (Miles Laboratories, Kankakee, IL).

EXAMPLE 7

PREPARATION OF RADIOACTIVE GTF ENZYME ANTIGENS

Sterile reconstituted protein hydrolysate ($^3$H) (5 mCi Schwartz/Mann, Orangeburg, N. J.) was added to 100 ml of the diolyzable BHI medium. Fifty milliliters of 10-fold concentrated non-radioactive culture supernatant were added to radioactive culture supernatant and the mixture was dialyzed extensively against PB. This material was subjected to DEAE-cellulose chromatography, as described for DE preparation, followed by filtration on a column of Sepharose 4B. The material, which constituted the GTF antigen used for the radioactive antigen-binding assay, eluted as a peak of radioactivity with REV of 2 and was coincident with a peak of enzyme activity. The specific activity of this material was 2180 cpm/µg lyophilized antigen. The material was 32% protein and 68% carbohydrate. Lowry O. H., J. N. Rosebrough, A. L. Farr, and R. J. Randall. 1951. Protein measurement with the Folin phenol reagent. *J. Biol. Chem.* 193:265; Dubois, M., K. A. Gilles, J. K. Hamilton, P. A. Rebers, and F. Smith. 1956. Colorimetric method for determination of sugars and related substances. *Anal. Chem.* 28.350. After electrophoresis of the antigen (4% polyacrylamide disc gel) and counting gel slices, more than 70% of the radioactivity of the material applied was found in a single peak. Cox, G. S., and T. W. Conway. 1975. Template properties of bacteriophage T4 vegetative DNA. I. Isolation and characterization of two template fractions from gently lysed T4-infected bacteria. *J. Biol. Chem.* 250:8926. Gel diffusion analyses of this material against the serums of G rats immunized with Antigen No. 2 or hamsters immunized with Antigens DE-1 or DE-2, revealed only a single identical Antigenic component.

EXAMPLE 8

ASSAY FOR INHIBITION OF GTF ACTIVITY

Two separate assays were used to detect antibody activity in the serums and salivas of rats immunized with Antigens Nos. 1 and 2. The first assay was used to demonstrate functional inhibition of GTF-medated glucose incorporation into total polysaccharide. Both serums and salivas of rats and hamsters taken prior to infection and at the termination of the experiment were analyzed. Before infection, the serums of rats immunized three or five times or hamsters immunized four times showed mean enzyme inhibition of from 52.4% to 59.2%. At termination, after the animals had been immunized 1 to 5 additional times, the level of serum inhibition was maintained in one experiment (P1), diminished about 10% in two experiments (P2, G1) and substantially raised in the hamster experiments. Both hydroxylapatite-prepared (Antigen No. 1) and the DEAE-cellulose-prepared antigens, (Antigen No. 2) elicited similar levels of inhibitory activity in the rat experiments. The serums of shamimmunized rats and hamsters showed no significant effect on enzymatic activity.

Salivas of pathogen-free and gnotobiotic rats immunized with Antigen No. 1 also inhibited polysaccharide formation by GTF. Inhibition was from 7.9% to 12.3% with immune salivas taken before infection and from 5.3% to 30.6% with salivas taken at experiment termination. Although reductions in $^{14}$C-glucose incorporation into ethanol-insoluble polysaccharide were low, immune (group IV) salivary inhibition was always greater than that occurring in the salivas of sham-immunized animals (group III), in both rat models. In experiment P1, sham-immunized animals' saliva taken at experimental termination showed 12.5% inhibition of GTF activity. This may be due to the extensive period of infection in this experiment (119 days) which may have resulted in production of salivary antibody to the infecting organism. In the hamster saliva both defined enzyme antigens (DE-1 and DE-2) elicited measurable GTF-inhibiting activity following four injections in the salivary gland region. The difference between the mean inhibition by salivas of hamsters injected with DE-1 or DE-2 was not statistically meaningful. Inhibition was seen when these salivas were assayed against ammonium sulfate precipitated enzyme, against crude enzyme obtained by ion exchange chromatography and gel filtration, or against defined enzyme (DE-1).

The procedure for determining inhibition of glucosyltransferase activity by serum and saliva, a modification of the method of Evans and Genco (Evans, R. T., and R. J. Genco. 1973. Inhibition of glucosyltransferase activity by antisera to known serotypes of *Streptococcus mutans. Infect Immun.* 7:237), has been described previously (Smith, D. J., and M. A. Taubman. 1977. Antigenic relatedness of glucosyltransferases from *Streptococcus mutans. Infect. Immun.* 15: 91-103). GTF activity was measured by determining $^{14}$C-glucose incorporation from glucosyl-labeled sucrose into ethanol-insoluble polysaccharide which contains both water-insoluble and ethanol-insoluble polysaccharide. Inhibition of GTF activity was expressed as the percentage reduction in amounts incorporated into precipitated polysaccharide by enzyme in the presence of immune serums (salivas) compared with incorporation by enzyme in the presence of control serums or salivas (usually from group I; group III in experiment G1). The mean counts±standard error (S.E.) incorporated by various enzyme preparations in the presence of control serums ranged from 1315±52 to 4494±170 in the experiments described hereinafter. For all experiments, the mean percentage difference of the counts incorporated in the presence of individual control serums from the mean of all control serums was 4.9%. The mean counts±S.E. incorporated by enzyme in the presence of control saliva ranged from 2987±73 to 8594±289. For all experiments the mean percentage difference of the counts incorporated in the presence of individual control salivas from the mean of all control salivas was 4.3%.

Inhibition of the two enzyme preparations used for assay (ammonium sulfate precipitated culture supernatant enzyme or Antigens as disclosed earlier) by the same serums from immunized rats and hamsters, did not differ by more than 2.4%. That inhibition in these assays reflects specific antibody activity has been demonstrated by using purified IgG anti-GTF actibody. Russell, M. W., S. J. Challacombe, and T. Lehner; Smith, D. J. and M. A. Taubman, both supra. In addition, specific precipitation and removal of IgA immunoglobulin from immune saliva left insignificant inhibitory activity. Genco, R. J., R. T. Evans, and M. A. Taubman, supra.

EXAMPLE 9

RADIOACTIVE GTF ANTIGEN BINDING ASSAY

The second assay used to detect antibody was the measurement of the radioactive antigen-binding capacity in serum and saliva (Table I below). This assay was used to confirm the antibody nature of the GTF-inhibitory activity in rat serum and saliva and to determine the classes of antibody of this specificity in saliva. Since previous studies showed that the principal *S. mutans* agglutinating antibody in rat serum was of the IgG class (Taubman, M. A., and D. J. Smith Infect. Immun. 9:1079, supra.), rat serum IgG GTF-binding activity was precipitated with excess rabbit-anti-rat IgG. Little binding of radiolabeled GTF was observed by serums of control rats in pathogen-free or gnotobiotic rat models. However, serums of antigen-immunized rats displayed significant GTF binding which could be attributed to IgG antibody. Salivas were also assayed for binding activity using excess rabbit antiglobulin reagent directed to rat IgA. Antibody of the IgA class, directed to GTF could be detected in immune rat salivas both before infection and at experiment termination. Although the binding levels were low, values were always higher than sham-immunized controls. IgG antibody was also detected in salivas of immunized gnotobiotic rats on day 53 and day 93(191±33 ng and 162±32 ng GTF bound/ml, respectively), indicating that these enzyme antigens elicit salivary antibody in both IgA and IgG classes when the rats are immunized in the salivary gland region. In general, the levels of GTF inhibition (functional assay) in both serum and saliva could be related to the levels of radioactive GTF bound, e.g., in experiment G1 the serums taken before infection showed 66.9% and 51.5% inhibition and 225 μg and 242 μg GTF bound/ml of serum, respectively. Salivas taken at the same time showed 295 ng and 13 ng GTF antigen bound by IgA/ml, and 223 ng and 158 ng GTF antigen bound by IgG/ml saliva. Inhibitions by these salivas were 8.4% and 7.3%, respectively.

Levels of binding of the radiolabeled GTF preparation were highest with serums or salivas from experiment G1. The radioactive antigen used for assay was prepared at the same time as the CE-2 preparation used for immunizing the gnotobiotic rats. Others serums from animals which had been immunized with other similar antigen preparations obtained in a like manner, were analyzed retrospectively, i.e., after storage for periods up to 1.7 years. These factors may account for the lower levels of binding in experiments P1 and P2.

TABLE I

Specific Radiolabeled-GTF Binding by IgG or IgA from Serum and Saliva of Rats

| Experiment | Day of Collection | Group (N) | Antigen | Serum (μg GTF bound by IgG/ml)[a] | Saliva (ng GTF bound by IgA/ml)[a] |
|---|---|---|---|---|---|
| P1 | 71 | III(4) | CFA + PBS | NT[b] | 0 ± 0 |
|  |  | IV(10) | CFA + CE-1 | NT | 67 ± 18 |
|  | 193 | III(6) | CFA + PBS | 2.8 ± 2.4 | NT |
|  |  | IV(11) | CFA + CE-1 | 67.2 ± 14.7 | NT |
| P2 | 64 | III(6) | CFA + PBS | NT | 15 ± 7 |
|  |  | IV(19) | CFA + CE-2 | NT | 28 ± 21 |
|  | 168 | III(6) | CFA + PBS | 1.3 ± 0.6 | 10 ± 5 |
|  |  | IV(22) | CFA + CE-2 | 16.1 ± 1.9 | 14 ± 3 |
| G1 | 53 | III(1) | CFA + PBS | 0 | 0 |
|  |  | IV(2) | CFA + CE-2 | 248.8 ± 6.5 | 154 ± 141 |
|  | 93 | III(6) | CFA + PBS | 1.2 ± 0.5 | 8 ± 3[c] |
|  |  | IV(6) | CFA + CE-2 | 219.3 ± 22.8 | 54 ± 15[c] |

[a]Expressed as group mean ± standard error.
[b]NT, not tested
[c]Five salivas tested in each group on this occasion, (N = 5)

The antigen-binding capacities of serum and saliva samples and the relative contribution of IgG and IgA were determined by a modification of the method described by Waldman and Henney. (Waldman, R. H., and C. S. Henney. 1971. Cell-mediated immunity and antibody responses in the respiratory tract after local and systemic immunization. J. Exp. Med. 134.482) Excess radioactive antigen was added to 5 μl of the test serum. After incubation at 37° C. for 4 hr. an excess (50 μl) of the rabbit-anti-rat IgG globulin reagent was added which caused total precipitation of the IgG. The precipitates were incubated overnight at 4° C. and were washed three times with cold PBS. The precipitates were solubilized with 0.25 N NaOH, neutralized and counted in Ready-Solv Solution VI. The counts per minute recorded were corrected for normal serum controls (serums from animals of group I) and tabulated as the amount of antigen (micrograms) that was bound by IgG in 1 ml of serum.

Individual saliva samples (140 μl) were incubated with an excess of radioactive antigen at 37° C. for 3 hr, after which 5 µl of normal serum was added to provide IgG for coprecipitation with the salivary IgG. The remainder of the procedure is identical to the procedure for the serum IgG-binding determination described above. Salivary IgA-binding was determined on separate samples to which the radioactive antigen had been added (37° C. for 3 hr) followed by an excess (10 µl) of the rabbit-anti-rat IgA globulin and incubation at 4° C. overnight. No precipitate was visible. Sufficient goat anti-rabbit IgG serum was then added to precipitate the rabbit IgG antibody which had bound the rat salivary IgG-GTF complexes. These reagents were incubated at 37° C. for 2 hr and at 4° C. for 2 hr. The ensuing precipitates were treated as described above. Knowledge of the specific activity of the GTF preparation permitted calculation of the nanograms of antigen bound by IgA antibody per milliliter of rat saliva. The reproducibility of the serum IgG radioactive antigen-binding assay was tested by repeating the assay more than 2 months apart.

The mean percentage of difference between salivary replicates was 2.6% and 6.1% for IgA and IgG, respectively.

EXAMPLE 10

BACTERIAL STUDIES

Since antibody activity in serum and saliva could be raised by local injection of rats or hamsters with CE-1 or CE-2 or defined enzyme antigens, it was of interest to determine the effect of this immunization on the colonization of pathogenesis of cariogenic streptococci. Therefore, all groups but group I control animals in each model were infected with a strain of *S. mutans* 6715 which was both cariogenic and streptomycin resistant. The extent of *S. mutans* infection was qualitatively estimated by systematic swabbing of molar surfaces of infected P, G and H experimental animals at intervals throughout the infection period. In all experiments, fewer *S. mutans* were recovered from immunized rats or hamsters on all but one swabbing occasion (Table II). The numbers of colony-forming bacterial units at experimental termination, determined either by grinding the half jaw (P1) or by buccal and lingual plaque removal (P2, G1, H1) are also shown in Table II. In each experiment, the mean numbers in group IV (CE-immunized) showed reduction in the number of *S. mutans* when compared to the nonimmunized group II or to group III. However, in no experiment were the *S. mutans* colony-forming units derived from the dental surfaces of immune animals statistically lower when compared to the other infected groups. Thus, as seen previously when formalin-killed *S. mutans* were used for injection (Taubman, M. A. and D. J. Smith. 1974. *Infect. Immun.* 9:1079, supra) the results are only suggestive of reductions in plaque-associated *S. mutans* recovered from immunized animals. In the one experiment in which saliva was analyzed (G1) there were fewer *S. mutans* in group IV saliva than in group III. This could reflect agglutination of bacteria by immune saliva. However, the conditions employed for sonication rupture the non-covalent forces by which antibody agglutinates cells.

TABLE II

Bacterial Recoveries from Rats and Hamsters During Infection and at Experimental Termination

| | During Infection | | Experimental Termination | | | | |
|---|---|---|---|---|---|---|---|
| | Occasions when *S. mutans* recoveries by swabbing[a] from group IV were lower than from group III/total occasions | | | Days after infection | *S. mutans* × 10³ | | Total Colonies × 10⁶ |
| Exp. No. | | Group | | | Geo mean | (Range) | Geo mean (Range) |
| P1 | ⅔ | II | | | 827 | (15–5330) | 1850 (365–9950) |
| | | III | 119[b] | | 612 | (185–6680) | 479 (21–8710) |
| | | IV | | | 338 | (15–4210) | 454 (120–8500) |
| P2 | 2/2 | III | 100[c] | | 8 | (0.8–43) | 4 (0.08–14) |
| | | IV | | | 6 | (0.1–112) | 2 (0.01–39) |
| G1 | 2/2 | III | 40[d] | | 19 | (8–31) | |
| | | IV | | | 7 | (1–25) | |
| H1 | 2/2 | III | 39[c] | | 167 | (133–221) | 29 (22–38) |
| | | IVA | | | 102 | (31–382) | 18 (4–60) |
| | | IVB | | | 123 | (43–315) | 20 (8–52) |

[a]Procedure was performed 18, 30 and 52 days (P1), 7 and 38 days (P2), 7 and 30 days (G1) and 4 and 23 days (H1) postinfection.
[b]Colony-forming units (CFU)/half jaw. Total colonies recovered on blood agar plates.
[c]CFU/smooth surface plaque. Total colonies recovered on mitissalivarius agar plates without streptomycin.
[d]Only *S. mutans* 6715 recovered. Mean *S. mutans* CFU × 10⁵ recovered per milliliter of saliva; group III, 27(3–168), group IV, 10(3–60).

EXAMPLE 11

CARIES SCORES AND LESIONS

Previous studies in the P and G rat models have shown that the use of formalin-killed *S. mutans* cells as antigen could confer a measure of protection from dental disease caused by subsequent infection with cariogenic *S. mutans* cells as antigen could confer a measure of protection from dental disease caused by subsequent infection with cariogenic *S. mutans*. Taubman, M. A., and D. J. Smith, immediately preceding. To assess the effects of injection of CE and DE glucosyltransferase preparations derived from these organisms on such infection, the mean caries scores of each group in the P, G, and H experiments were determined (Table III). The immunized group IV always had lower mean caries scores than the other infected group or groups. These differences were statistically significant in three of the four experiments, including one experiment with each animal model employed. Hamsters immunized with either of the defined antigen preparations showed a somewhat higher level of protection than did CEinjected rats (to the limited extent of comparability of these animal models), and a similar level of protection when compared with each other. Weights of animals in experiments P1, P2, and H1 were monitored throughout each experiment and were not significantly different among all groups of animals on any occasion.

The limited level of caries found in non-infected groups (group I) of the conventional rat experiments was comparable to the level seen previously in rats maintained on a low carbohydrate diet (L-356) during the preinfection period. In one experiment (P2) the caries scores of immunized animals were slightly lower than the scores of uninfected animals. This difference was not statistically meaningful nor was it found when the lesions were examined (Table IV). As in the conventional rats, the hamsters showed a background of dental caries in noninfected controls. The uninfected group in the H experiment demonstrated about one-third of the caries of comparable group I rats. In the hamsters, the duration of infection was only 39 days and the animals' age at termination was 90 days. This infection period, however, was adequate to produce extensive caries in the sham-immunized (group III) hamsters. Differences in the extent of caries between P1 and P2 in the infected group are most likely the result of differences in the cariogenicity of the S. mutans used for infection.

The immune groups of the three different rodent models always demonstrated lower mean numbers of lesions than the other infected groups (Table IV). These reductions were statistically significant when compared with the other infected groups in three of four experiments. Similarities in the numbers of lesions in uninfected group I and CE-immunized group IV of the P rat experiments are reminiscent of the pattern of protection seen for rats immunized with whole organisms where this pattern was suggested to reflect interference with initiation of new lesions after infection. Taubman, M. A. and D. J. Smith, supra. The occurrence of lesions in the hamsters does not exactly follow this pattern because of the increased virulence of S. mutans in this hamster model and the lower background caries. However, it is clear that both immunized groups of hamsters demonstrated significantly fewer carious lesions than comparable sham-immunized controls. Therefore, the initiation of new lesions has been interfered with to some extent. The DE-1 antigen might be considered to elicit a slightly more protective immune response than DE-2 since the lesions seen in DE-1-injected animals were fewer than those seen in DE-2-injected animals (both of which were significantly lower than adjuvant-injected hamsters).

TABLE III

Mean Caries Scores of Immunized and Control Rats and Hamsters

| Treatment | Group | P1(CE-1)[a] | P2(CE-2) | G1(CE-2) mean caries scores[b] | H1(DE) |
|---|---|---|---|---|---|
| Noninfected, nonimmunized | I | 12.2 ± 3.4 | 12.6 ± 1.4 | | 4.6 ± 0.7[c] |
| Infected, nonimmunized | II | 35.3 ± 10.0 | | | |
| Infected, sham-immunized | III | 33.0 ± 9.5 | 16.7 ± 1.6 | 17.8 ± 3.1 | 47.3 ± 10.3 |
| Infected, immunized | IV | 21.9 ± 5.5 | 10.9 ± 1.2[d] | 7.4 ± 1.1[d] | |
| | IVA(DE-1) | | | | 15.4 ± 1.9[c] |
| | IVB(DE-2) | | | | 17.4 ± 2.5[c] |

[a]Experiment (antigen used for immunizing group IV)
[b]Group means and standard errors; each rat group represents the scores of at least six animals, hamster group III, four animals, other hamster groups; I (5), IVA (12), and IVB (12). Caries scores were obtained by a modified Keyes method, supra.
[c]Statistically signifcant, $p < 0.001$
[d]Statistically significant, $p < 0.01$

TABLE IV

Mean Numbers of Carious Lesions of Immunized and Control Rats and Hamsters

| Treatment | Group | P1(CE-)[a] | P2(CE-2) | G1(CE-2) mean nos. of carious lesions[b] | H1(DE) |
|---|---|---|---|---|---|
| Noninfected, nonimmunized | I | 20.0 ± 1.8[c] | 17.0 ± 1.0[d] | | 8.2 ± 1.9[c] |
| Infected, nonimmunized | II | 27.9 ± 2.3 | | | |
| Infected, sham, immunized | III | 28.0 ± 4.0 | 20.8 ± 1.0 | 21.5 ± 2.9 | 42.0 ± 6.4 |
| Infected, immunized | IV | 24.9 ± 2.4 | 17.8 ± 1.0[c] | 13.7 ± 1.4[c] | |
| | IVA(DE-1) | | | | 21.2 ± 4.5[e] |
| | IVA(DE-2) | | | | 24.3 ± 1.9[f] |

[a]Experiment (antigen used for immunizing group IV).
[b]Group means and standard errors, each rat group represents the numbers of lesions of at least 6 animals; hamster group III, 4 animals, other hamster groups: I(5), IVA(12), and IVB(12). Carious lesions, evaluated by a modified Keyes method, were scored as the number of sites of disease on each molar surface.
[c]Statistically significant, $p < 0.05$.
[d]Statistically significant, $p < 0.01$.
[e]Statistically significant, $p < 0.001$.
[f]Statistically significant, $p < 0.005$.

The caries scores and lesions of GTF-immunized and control animals were determined with respect to surface. The scores and lesions of the sham-immunized Group III animals were then compared with those of the corresponding Group IV animals by calculating the percentage reductions of immune vs sham (Table V). Reductions in both parameters were always seen in immunized animals on both occlusal, and smooth (buccal and lingual) surfaces. The smooth surfaces examined displayed the greatest reduction in number of lesions in every experiment. In all experiments, except P2, smooth surface reductions also were predominant when caries scores were compared. This pattern supports the concept that an interference with the production of new lesions, primarily on smooth surfaces, has occurred in immunized animals.

TABLE V

Reduction of Caries Scores or Lesions on Occlusal or Smooth Surfaces of Immunized Rats and Hamsters Compared with Control Rats and Hamsters

|    |           |          | Percentage Reduction |         |         |         |
|    |           |          | Caries[a]            |         | Lesions[b] |      |
|    | Model     | Antigen  | Occlusal Surface | Buccal & Lingual Surface | Occlusal Surface | Buccal & Lingual Surface |
|----|-----------|----------|------|------|------|------|
| P1 | Pathogen-free rat | CE-1 | 24.2 | 50.2 | 10.6 | 24.7 |
| P2 | Pathogen-free rat | CE-2 | 36.8 | 22.9 | 17.7 | 44.4 |
| G1 | Gnotobiotic | CE-2 | 54.8 | 100 | 19.6 | 100 |
| H1 | Hamster | DE-1 | 56.5 | 79.5 | 39.1 | 62.8 |
|    |           | DE-2 | 50.5 | 77.2 | 31.4 | 55.9 |

[a] 100 - ((Mean caries score of group IV)/(mean caries score of group III) × 100).
[b] 100 - ((Mean number of lesions of group IV)/(mean number of lesions of group III) × 100).

The experiments set forth in the above examples, (Examples 1–11), have been disclosed in *The Journal of Immunology*, Vol. 118, No. 2, pp 710–720, Effects of Local Immunization With Glucosyltransferase Fractions from Streptococcus Mutans on Dental Caries in Rats and Hamsters, incorporated herein by reference.

Previous studies have shown that local immunization of either conventional or gnotobiotic rats with particulate *S. mutans* antigens (formalinized whole cells) gave rise to primarily a salivary IgA response after local immunization. Taubman, M. A. 1973. Taubman, M. A. and D. J. Smith 1974, both supra. In these studies rats demonstrating a salivary IgA response were shown to have less caries than comparable sham-immunized control animals. In the experiments described in the above examples, soluble preparations of GTF antigens in various stages of purification were used for local immunization after incorporation into complete Freund's adjuvant. In those gnotobiotic animals where the response was studied, IgG and IgA salivary antibodies were both present after three or five injections of CE. While some have suggested that IgA is the only major Ig in rat saliva, (Bistany, T. S., and T. B. Tomasi, Jr. 1970. Serum and secretory immunoglobulins of the rat, *Immunochemistry* 7:453), qualitative studies have indicated that IgA is present in slightly higher concentration than IgG2 (McGhee, J. R., S. M. Michalek, and V. K. Ghanta, 1975. Rat immunoglobulins in serum and secretions: purification of rat IgM, IgA and IgG and their quantitation in serum, colostrum, milk and saliva. *Immunochemistry*. 12:817. Thus, in any study where CFA is utilized for local stimulation it is not surprising to find both IgA and IgG antibodies in the saliva of an animal that has approximately equal amounts of these immunoglobulins. Some of the salivary IgG may be serum derived, but it is clear in the rabbit, and probably in the rat, that both the IgG and IgA can be locally synthesized in the salivary glands. (Taubman, M. A., G. G. Emmings and R. J. Genco, 1970. Production of antibodies and immunoglobulins by rabbit salivary glands. J. Dent. Res. 49(Special Issue):70. Hurlimann, J., and H. Darling. 1971. In vitro synthesis of immunoglobulin A by salivary glands from animals of different species. Immunology 21:101.)

It has been our contention that salivary antibody is the most likely protective principle in relation to experimental dental caries in rodent models. In humans, IgA is the major immunoglobulin in the oral cavity, (Brandtzaeg, P., I. Fjellanger, and S. T. Gjeruldsen. 1970. Human secretory immunoglobulins. I. Salivary secretions from individuals with normal or low levels of serum immunoglobulins. *Scand. J. Haematol.* (Suppl.) 12:1), and the suggestion has been made that human IgA can function to interfere with the interactions necessary for plaque formation. Taubman, M. A., and D. J. Smith. 1976. Immune components in dental plaque, *J. Dent. Res.* 55 (Special Issue C):C153. There may be a significant correlation between high caries experience and a low IgA secretion rate. Orstavik, D., and P. Brandtzaeg. 1975. Secretion of parotid IgA in relation to gingival inflammation and dental caries experience in man. *Arch. Oral Biol.* 20:701. Furthermore, recent experiments of Michalek and her colleagues (Michalek, S. M., J. R. McGhee. J. M. Mestecky, R. R. Arnold, and L. Bozzo. 1976. Ingestion of *Streptococcus mutans* induces secretory immunoglobulin A and caries immunity. *Science* 192:1238) demonstrated that salivary antibody alone can be protective with respect to dental caries. Only a salivary IgA response could be detected when gnotobiotic rats were fed killed *S. mutans* whole cells, as we have also observed. Taubman, M. A., and D. J. Smith. 1973. Induction of salivary IgA antibody in rats and hamsters. *J. Dent. Res.* 52 (Special Issue):276. In the absence of detectable serum antibody significant reductions in dental caries were shown after infection with *S. mutans*. Michalek, S. M., J. R. McGhee et al, supra. Therefore, it appears that salivary antibody, alone, can be protective with regard to dental caries.

In the rodent model described in the above examples, it would seem reasonable to assume that the combination of salivary IgG and IgA antibodies functions in a manner similar to IgA in human saliva. In these rodent experiments we have not only shown binding of radioactive glucosyltransferase (GTF) enzymes by serum and salivary antibody, but we have also shown that immune serums and salivas could inhibit the function of these enzmes. Some contention exists as to the ability of nonimmune serum or oral fluid (Burckhardt, J. J., and B. Guggenheim. 1976. Interactions of antisera, sera and oral fluid with glucosyltransferases. *Infect. Immun.* 13:1009. and Russell, M. W., S. J. Challacombe, and T. Lehner, supra.) to enhance GTF activity when compared to enzyme preparations in buffer in the assay we have employed. Although such may be the case, due to interaction and stabilization or possibly primer function, it is clear that if proper controls are included, this assay is sensitive, reproducible and measures antibody. Also of interest is the suggestion that human secretory IgA which is not antibody to GTF, may enhance the activity of some types of GTF. Pukui, K. Y. Fukui, and T. Moriyama. 1974. Acceleration of dextransucrase activity of *Streptococcus mutans* by secretory immunoglobulin A. *J. Bacteriol.* 118:805. Purified rat secretory IgA does not significantly enhance GTF activity in the assay we routinely perform. Inhibition of the function of GTF enzymes is particularly important since these enzymes have been implicated in the expression of the pathogenic potential of cariogenic *S. mutans*. Evidence strongly suggests that the ability of this microorganism to adhere to the tooth surface, and participate in the formation of dental plaques, depends on the synthesis of extracellular glucose polymers from sucrose. Gibbons R. J. and J. van Houte, supra. Recently, Michalek and her coworkers (Michalek, S. M., T. Shiota, T. Ikeda, J. M. Navia, and J. R. McGhee. 1975. Virulence of *Streptococcus mutans*: Bio chemical and pathogenic characteristics of mutant isolates. *Proc. Soc. Exp. Biol. Med.* 150:498) have been able to relate the synthesis of water-insoluble glucan (by GTF) and in vitro adherence directly to the cariogenicity (virulence) of *S. mutans* mutanta. They showed that mutants, synthesizing increased amounts of water-insoluble polysaccharide, demonstrated increased adherence and greater cariogenicity than wild type organisms. These studies emphasize the highly significant role of the GTF of *S. mutans* in the expression of their virulence.

Previously we have suggested that two likely antigens of *S. mutans* for immunization experiments might be either the serotype-specific carbohydrate antigen or the GTF enzymes. Smith, D. J., and M. A. Taubman. 1976. Immunization experiments using the rodent caries model. J. Dent. Res. 55 (Special Issue C):C193. This suggestion was based on the demonstration that antibody directed to either of these antigens had the capacity to interfere with adherence phenomena demonstrated by *S. mutans in vitro*. Mukasa, H., and H. D. Slade. 1974. Methanism of adherence of *Streptococcus mutans* to smooth surfaces. II. Nature of the binding site and the adsorption of dextran-levan synthetase enzyme on the cell wall surface of the streptococcus. *Infect. Immun.* 9:419, Iacono, V. J., M. A. Taubman, D. J. Smith, P. R. Garant, and J. R. Pollock. 1976. Structure and function of the type-specific polysaccharide of *Streptococcus mutans* 6715. *Immunology Abstracts* (Special Suppl.):75. Although both antigens occur in culture supernatants, in the current invention, we have been careful to eliminate type-specific antigen from all our GTF preparations used for immunization. Antibody reactive with the type-specific antigen was never detected in the serums of any of the animals immunized with these enzyme preparations. The levels of protection reported in the above examples, utilizing CE-1 and CE-2 GTF as an antigen in the rat models, are quite comparable to the levels of protection obtained previously after immunization with whole cells. Taubman, Smith, supra. The experiment in hamsters with more defined GTF enzymes (DE-1 and DE-2) as immunogens also supports the contention that GTF enzyme is of major importance as antigen. Although the evidence is not unequivocal, there are several additional compelling reasons in support of the case for GTF enzyme: (a) Other enzyme antigens (e.g., fructosyltransferase or invertase) were probably absent from our GTF fractions. (b) Both GTF enzyme preparations, having only one enzyme antigen in common, gave rise to protection. (c) Although the DE-1 preparation contained trace amounts of material reactive with an antiserum directed to the polyglycerol phosphate (PGP) backbone of teichoic acid, as did DE-2, serum antibody from hamsters immunized with either of these preparations did not react with teichoic acid from *S. Sanguis*. (d) Immunized animals showed antibody in serum and saliva which would bind and inhibit GTF activity. (3) The likelihood of DE-1 and DE-2 containing common antigens other than enzyme is low due to the complex series of procedures followed and the purposeful selection for material demonstrating enzyme (GTF) activity. Nevertheless, it is clear that even more purified enzyme as antigen would better establish the importance of GTF in the pathogenesis of *S. mutans* and also the importance of GTF as antigen for immunization.

The use of purified antigens for immunization with *S. mutans* is also important for other reasons. Van de Rijn and his colleagues (Van de Rijn, I., A. S. Bleiweis, and J. B. Zabriskie, 1976. Antigens in *Streptococcus mutans* cross reactive with human heart muscle. *J. Dent. Res.* 55(Special Issue C):C59.) have apparently demonstrated, by indirect immunofluorescent staining, that the serums of rabbits inoculated intravenously with *S. mutans* contain antibody reactive with human myocardium. The type of fluorescent staining appears to resemble that seen both after injection of rabbits with group A streptococcal membranes and with acute rheumatic fever patients' serums. Indeed, human heart reactive antibody in the serums of *S. mutans* immunized rabbits could be removed by adsorption with group A streptococcal membranes. Although the significance of this type of antibody has never been established, and no direct evidence exists that these antibodies are cytotoxic, it is conceivable that antibody directed to *S. mutans* organisms could play a role in the pathogenesis of rheumatic fever. Although it is quite unlikely that GTF is an important antigen in the induction of heart reactive antibody, (group A streptococci do not possess these cell-bound enzymes), serums from animals immunized with GTF will have to be examined for the presence of heart reactive antibody.

The exact mechanism whereby antibody can interfere with the molecular pathogenesis of dental caries caused by *S. mutans* is not completely understood. However, the following suggestions are consistent with current knowledge: We will consider that there are essentially two types of GTF enzymes (one type synthesizing water-soluble product and the other type synthesizing water-insoluble product). In the presence of sucrose, enzyme synthesizing water-soluble product initiates synthesis of dextran-like polymer extracellularly. Mukasa, H. and H. D. Slade. 1973, 1974, both supra. It is clear that a receptor(s) exist on *S. mutans* which can specifically bind dextran (Spinell, D. M. and R. J. Gibbons, 1975; Mukasa, H. and H. D. Slade, 1974, and Iacono, V. J., M. A. Taubam, D. J. Smith, P. R. Garant, and J. R. Pollock, spura. Dextran synthesized by GTF can bind to the receptor(s) for dextran. GTF, which can also bind dextran, can then join the cell-associated GTF-dextran complex. Since sucrose is present, the GTF can then initiate synthesis of mutan (Water-insoluble product) by using the dextran as a primer for added glucose molecules or by direct synthesis. Germaine, G. R., A. M. Chludzinski, and C. F. Schachtele. 1974. *Streptococcus mutans* dextransucrase: requirement for primer dextran. *J. Bacteriol.* 120:287. The active synthesis (Mukasa, H. and H. D. Slade, supra) of mutan is necessary for the organism to manifest adherence to hard surfaces. Disruption of dextran synthesis could also affect the ability of *S. mutans* to agglutinate. This parameter may also be of significance in dental plaque formation. Therefore, interference with either dextran or mutan-synthesizing GTF by antibody should theoretically result in reductions in the bacterial masses adherent to the teeth. This in turn would result in less secretion of acid end-products and less tooth demineralization. Such reductions in caries compared to appropriate controls were found in all experiments in which animals were immunized with GTF.

While the suggestion has been made that the water-insoluble polysaccharide (mutan) is more significant in *S. mutans* pathogenesis than the soluble polysaccharide (Michalek, S. M., T. Shiota, T. Ikeda, J. M. Navia, and J. R. McGhee, supra.), and our data in the H1 experiment suggest a higher level of protection with DE-1 antigen, it is clear that antibody elicited by the DE-2 preparation is also protective. Therefore, at this stage it would seem to be premature to exclude one or another type of GTF activity from consideration as antigen.

Recently we have concluded from studies of the antigenic relatedness of GTP enzymes, using numerous immune serums and salivas, that two or at most three antigenically distinct subsets of GTF enzymes exist among the serotypes of *S. mutans*. Smith, D. J. and M. A. Taubman, 1977, supra. Therefore, it is conceivable that enzyme preparations from a limited number of representative serotypes could be used to provide protection against all serotypes. Furthermore, it may be possible to present these antigens in such a fashion as to provide stimulation of cellular elements both in minor salivary glands (Crawford, J. M., M. A. Taubman, and D. J. Smith. 1975. Minor salivary glands as a major source of secretory immunoglobulin A in the human oral cavity. *Science* 190:1206) and in gut-associated lymphoid tissue (Michalek, S. M., J. R. McGhee, J. Mestecky, R. R. Arnold and L. Bozzo, supra), in order to elicit a protective response.

Immunization with somewhat crude glucosyltransferase preparations has resulted in significant reduction in experimental dental caries in rodents. However, these preparations, derived from culture supernatants have usually contained both water-soluble and water-insoluble glucan synthetic activity, together with several non-enzyme antigens. In order to identify GTF as the critical antigen in *in vivo* protection and crossprotection, and to evaluate the protective effect of GTF which is responsible for the synthesis, of water-insoluble glucan, the following technique was devised for GTF preparation.

EXAMPLE 12

PURIFICATION OF GLUCOSYLTRANSFERASE ANTIGEN BY RECOVERY FROM POLYSACCHARIDE

To prepare GTF synthesizing mutan, i.e., water insoluble glucan, cultures of *Streptococcus mutans* serotype a (strain E49), serotype c (strain Ingbritt) or serotype q (strain 6715) were grown in dialyzed BHI medium containing 1% glucose or a completely defined synthetic media also containing glucose for 20 hrs. at 37° C. The cells were removed by centrifugation according to usual techniques, and the culture supernatants were then incubated at 37° C. with 10% sucrose at pH 6.5, together with 0.02% sodium azide and 0.04 M salts. The water-insoluble polysaccharide in each supernatant formed was collected by centrifugation, washed (6×PBS; 6×dist. H₂O (and incubated at 4 C for 1 hr. with stirring in one to two times its volume in 6 M guanidine-HCl, to remove the portion of GTF which synthesizes mutan and which remains non-covalently bound to the polysaccharide. The polysaccharide was then removed by centrifugation, the guanidine was removed from the supernatant by dialysis with 0.05 M Na phosphate and the GTF in the supernatant was then enriched by gel filtration, as hereinafter disclosed.

Other denaturing solvents other than guanidine-HCl can be used, if desired, for example, urea and sodium dodecylsulfate. However, guanidine HCl has been found quite satisfactory in the practice of the invention. A relatively high concentration of solvent should be used, but from a practical aspect, a concentration of from 1:1 to 2:1 is most desired.

EXAMPLE 13

TIME COURSE OF THE RELEASE OF ENZYMATIC ACTIVITY

To determine the time course of the release of enzmatic activity when water-insoluble polysaccharides are exposed to guanidine-HCl, separate 10 gm polysaccharide samples were incubated with the denaturant for time periods ranging from 10 nutes to 70 hours. After removal of the polysaccharide, enzymatic activity in the dialyzed supernatants was determined by the release of total reducing sugars and glucose after incubation with sucrose. Little change occurred in the amount of activity released from strain E49 polysaccharide at the various times tested. Activity released from polysaccharide of strain 6715 increased until 20 hours and plateaued thereafter. Strain Ingbritt showed the greatest rate of change in release of GTF activity. Increasing amounts of activity were released through approximately 30 hours of incubation.

In each strain, the ratio of dextransucrase units released/ml., released at 1 and 20 hours, was similar to a ratio of the amount of glucan synthesized (determined radioisotopically) at these two times, indicating that the chemical assays were indeed reflecting GTF activity. Thus, GTF is released from water-insoluble polysaccharide from the three serotypes tested, albeit at differing rates. This difference may be dependant on chain length, amount or extent of branching, or the variety and ratio of linkages in the respective polysaccharides, as well as variations in the enzymes themselves.

EXAMPLE 14

RATIO OF CARBOHYDRATE TO PROTEIN RELEASED DURING EXPOSURE POLYSACCHARIDE TO GUANIDINE

Since guanidine might also have a disruptive effect on the structure of polysaccharide itself, samples were also analyzed for Lowrey protein and for carbohydrate by the method of Dubois, both supra. Accordingly, the ratio of CHO to protein released at various time intervals for strain 6715 was determined. At relatively short periods of incubation, it was found that protein represents one half to two thirds of the material in the supernatant. However, carbohydrate becomes the predominant component released at incubation periods longer than about 8 hours. Immunodiffusion analyses of this supernatant with purified antibody directed to glucan of the homologous strain, suggested that at least a proportion of this CHO is glucan.

EXAMPLE 15

ENRICHMENT OF GTF FROM *S. MUTANS* 6715

*S. mutans* strain 6715 GTF was selected for enrichment since this strain demonstrated little fructosyltransferase activity. After dialysis and concentration, the GTF-containing supernatant was gel filtered according to usual techniques on 8% agarose. Enzymatic activity in the elutions was determined by the Somogyi assay, supra. All enzymatic activity eluted (optical density 280 nm) at the void volume of the 8% agarose-column. The enzyme-containing fractions were then gel filtered on 2% agarose. Again most of the material eluted in one peak near the void volume and contained the enzymatic activity.

EXAMPLE 16

PROPERTIES OF GTF ENZYME RECOVERED

The properties of the enzyme contained in this peak are tabulated below.

| Properties of 6M GuHCl-Eluted GTF (strain 6715) Following Gel Filtration on 8% and 2% Agarose | |
|---|---|
| Specific Activity (U/mg) | 2.7 |
| Total U | 5.4 |
| Product | Insoluble |
| GTF/FTF (Incorporation of $^{14}$C-glucose and $^3$H-fructose from sucrose) | >97 |

The pool had a rather high specific activity. A total of 5.4 Units were contained in the pool. When enzyme was incubated with sucrose, only insoluble polysaccharide could be detected spectrophotometrically. Radioactive incorporation assays indicated that the polysaccharide formed was virtually all glucan. Thus the enzyme recovered could be characterized as glucosyltransferase forming only water-insoluble glucan.

The pool was also electrophoresed on duplicate 5% disc gels. After electrophoresis at 4 ma/gel for 1 hour, one gel was stained for protein with Amido Black and the other gel was incubated with sucrose to determine zones of mutan-synthetic activity. Only one band of protein and one corresponding area of enzymatic activity were seen, both migrating the same small distance from the origin.

The 2% agarose pool was also examined for antigenic components in immunodiffusion. The GTF pool was placed in the central well. Antisera to the serotype q antigen, to teichoic acid, to the glucan of S. mutans strain 6715, and to a crude enzyme antigen preparation from culture supernatants of the 6715 strain were placed in the outer wells. No serotype antigen or teichoic acid could be detected in the enzyme preparation according to the invention. However, a precipitin band did form with the anti-glucan antiserum. The anti-CEA antiserum reacted predominantly with one component, forming a precipitin band close to the antigen wall. This precipitating system migrated in immunoelectrophoretic analyses to the same region as the water-insoluble synthetic activity, identified in a separate run when sucrose was added to the trough. This indicated that the band seen in gel diffusion against the anti-CEA serum contained GTF. Thus, the guanidine-eluted and gel-filtered GTF pool seems to contain one protein component which is enzyme and one carbohydrate component which is glucan.

In order to determine the effect on enzymatic activity of antibody directed to this glucan, the serum from a rat injected twice with guanidine-eluted GTF 6715 was tested against the homologous enzyme preparation in a radioisotopic assay of GTF activity. The serum was either unabsorbed or was absorbed with twice its volume of Sephadex G-25, a predominantly α1-6 linkglucan. Both absorbed and unabsorbed antisera showed essentially the same level of inhibition, indicating that antibody directed to this type of glucan did not affect GTF activity as measured in the assay. This was supported by the observation that rabbit antibody directed against surface glucan of formalin-killed cells 6715 showed no significant inhibition. These results are shown below.

| Effect of Anti-Dextran Antibody on Inhibition of 6M GuHCl-Eluted GTF (GuGTF) Activity | | |
|---|---|---|
| Antiserum | Adsorbant | % Inhibition[b] of GuGTF |
| Rat anti-GTF$_{6715}$ | none | 31.2 ± 4.8 |
| Rat anti-GTF$_{6715}$ | G25 | 37.2 ± 4.5 |
| Rabbit anti-glucan$_{6715}$[a] | none | 2.2 ± |

[a]Ig released (pH 2.3) from G 25 following incubation with antisera directed to formalin-killed S. mutans 6715 cells
[b]Based on $^{14}$C-glucose incorporation from labeled sucrose into EtOH-insoluble polysaccharide compared to normal sera.

The ability of guanidine-eluted GTP to elicit a serum and secretory immune response was determined as follows. Fluids from hamsters and rats injected with complete Freund adjuvant (CFA) or with CFA plus guanidine-eluted GTF from serotype a E49 or from serotype q 6715 were evaluated for inhibition of enzymatic activity. Fluids from adjuvant-injected animals incorporated essentially the same level of $^{14}$C into EtOH-insoluble polysaccharide as did control sera or salivas. However, GTF from either strain gives rise to a significant inhibitory response in serum when tested against the homologous enzyme. In addition, sera from these GTF-immunized animals inhibited enzyme from serologically related strains at least as well as the homologous strain. Importantly, a significant salivary inhibitory response was also elicited by this enzyme preparation.

The ease of preparation, the restricted activity and the immunogenicity of purified enzyme population of the invention provides GTF that is highly satisfactory as a caries protective antigen.

| GTF Inhibitory Activity in Serum and Saliva of Rodents Immunized with GTF Eluted from Mutan with 6M GuHCl | | | | |
|---|---|---|---|---|
| | | | Inhibition Assay[c] | |
| GTF[a] Source | Antigen Preparation | Fluid (N) | GTF[b] Strain | Percentage Inhibition |
| E49 | CFA | Hamster Sera (9) | E49 | 0.1 ± 4.4 |
| | GTF + CFA | Hamster Sera (10) | E49 | 62.1 ± 3.8 |
| | GTF + CFA | Hamster Sera (4) | 6715 | 79.4 ± 1.8 |
| | CFA | Hamster Saliva (10) | E49 | 0.2 ± 1.8 |
| | GTF + CFA | Hamster Saliva | E49 | 12.8 ± 3.4 |
| 6715 | CFA | Rat Sera (6) | 6715 | 1.8 ± 3.6 |
| | GTF + CFA | Rat Sera (2) | 6715 | 34.2 ± 2.6 |
| | GTF + CFA | Rat Sera (2) | E49 | 35.0 ± 1.7 |

[a]GTF (eluted from mutan with 6M GuHCl) and/or complete Freund's adjuvant (CFA).
[b]55% (NH$_4$)$_2$SO$_4$ precipitated culture supernatant.
[c]Inhibition of 14C-glucose incorporation into EtOH-insoluble glucan compared to incorporation in presence of normal serum or saliva. Mean ± standard error.

Instead of the gel filtration on 2% agarose above disclosed, a phenyl sepharose column, equilibrated in 6 M guanidine HCl was also used. This procedure removes the glucan from the GTF. The material eluted has been found highly satisfactory.

Immunization experiments in the rodent model in which antigenic preparations containing GTF from serotypes b or q have clearly demonstrated protection from caries caused by infection with homologous strains of *S. mutans*. Hayashi, J. A., Shklair, I. L. and Bahn, A. N., *J. Dent. Res.* 51:436, 1972 and Taubman, M. A. and Smith, D. J., *J. Immunol.* 118:710, 1977. These lines of evidence seem to indicate that antibody directed to GTF antigens might product animals from caries caused by organisms from which the enzyme was derived (homologous). However, the protection afforded by such immunization against other strains or serotypes of *S. mutans* (heterologous) is unclear. *S. mutans* organisms are heterogeneous and are divided into from three to seven groups, based on serological, genetic or biochemical differences. Bratthall, D. and Kohler, B., *J. Dent Res.* 55:C15, 1976. Differing antigenic and biochemical features have also been noted among GTF preparations derived from the various serotypes, Genco R. J., Evans, R. T. and Taubman, M. A., *Adv. Exp. Med. Biol.* 45:327, 1975; Fukui, K., Fukui, Y. and Moriyama, T., *Infect. Immun.* 10:985, 1974; Linzer, R. and Slade, H. O., *Infect. Immun.* 13:494, 1976; Smith, D. J. and Taubman, M. A., *Infect. Immun.* 15:91, 1977; Kuramitsu, H. and Ingersoll, L., *Infect. Immun.* 14:636, 1976. However, by *in vitro* techniques antigenic similarities seem to exist among GTP from serotypes a, d, g and among GTP from serotypes b, c, e. The purpose of the present investigation was to determine to what extent these *in vitro* relationships might be reflected in *in vivo* protection. The protective and cross-protective effects of local immunization with GTF from *S. mutans* strain Ingbritt (serotype c), 6715 (serotype g) or E49 (serotype a), on infection with homologous organisms (serotype c) or infection with heterologous organisms (*S. mutans* strain 6715, serotype g of strain Ingbritt serotype c or strain E49 serotype a) was explored in the hamster model.

The following examples show the cross-protective aspece of glucosyltransferase antigens.

EXAMPLE 17

PREPARATION OF GTP

Strains of Streptococcus mutans strains E49 (serotype a), Ingbritt (serotype c) and 6715 (serotype g), known to be cariogenic in hamsters and resistant to streptomycin at concentrations of 200 μg/ml, were each grown anaerobically (10% $CO_2$, 90% $N_2O$) for 24 hours at 37° C. in 6 to 10 liters of synthetic media. After centrifugation (9000 rpm) each cell-free supernatant was pH-adjusted to 6.5. Polysaccharide was then synthesized in each supernatant by the addition of sucrose to 10% and incubation at 37° C. for 48 hours. Bacterial growth was inhibited by addition of 0.02% sodium azide.

The water insoluble polysaccharide which was formed in each supernatant was collected by centrifugation (9000 rpm) at 4° C. and washed extensively with cold distilled $H_2O$ and 0.01 M sodium phosphate, pH 6.8 to which 0.02% sodium azide had been added. Glucosyltransferase enzymes were then eluted from the washed, water-insoluble polysaccharides by one hour incubation (4° C.) with a volume of 6 M guanidine-HCl which was twice the weight of the polysaccharide, as reported previously. Smith, D. J., Taubman, M. A. and Ebersole, J. L., *J. Dent. Res.* 15:A132, 1977. Following elution, guanidine was removed by dialysis and, after concentration, the eluate was gel filtered on columns of 8% agatose in 0.01 M sodium phosphate, pH 6.8.

Enzyme activity from each strain was detected by the Somogyi (Somogyi, M., *J. Biol. Chem.* 160:61, 1945) and Glucostat (Worthington Biochemical) assays to elute at the void volume. Fructose was the principle sugar released with either serotype a (79%) or serotype c (75%) GTF. Neither GTF preparation contained teichoic acid or the serotype specific antigen, although glucan was detected when assayed with specific antisera in immunodiffusion. Guanidine-eluted GTF preparations from either serotype a or c formed water-insoluble and ethanol-insoluble polysaccharide when incubated with 0.12 M sucrose for 4 hours at 37° C.

EXAMPLE 18

IMMUNIZATIONS AND INFECTIONS

In all experiments, NIH white hamsters were divided into five groups, (1) nonimmunized and noninfected; (II) sham immunized with 0.1 ml PBS incorporated into 0.1 ml CFA and infected with serotype c strain Ingbritt (homologous infection); (III) sham immunized and infected with organisms from serotype g strain 6715 (heterologous infection); (IV) immunized with 0.1 ml Ingbritt GTF (containing 0.8 units of activity-12) in 0.1 ml CFA and homologously infected; (V) immunized with Ingbritt GTF in CFA and heterologously infected. This is hamster experiment 2(H2). In hamster experiment 3(H3) the injected GTF was from serotype a (E49) and homologous infection was with strain E49, while heterologous infection was with strain 6715 (serotype g). In hamster experiment 4(H4) the infected GTF was from serotype g (6715) and homologous infection was with strain 6715 (serotype g) and the heterologous infection was with strain Ingbritt (serotype c).

Four injections were given at 7 to 10 day intervals in the salivary gland vicinity (SGV) prior to infection and one injection was given midway in the 40 day infection period. All hamsters were maintained on Purina Mouse chow from weaning to three days prior to infection when diet 2000 was initiated. Keyes, P. H. and Jordan, H. V., *Archs. Oral Biol.* 9.377, 1964. The weights of the animals were not significantly different among the five groups of animals for the duration of the experiment.

The hamsters (H2) in groups II and IV, and groups III and V were orally infected with 0.4 ml of 20 hour cultures of S. mutans (approximately 10° colony forming units) strains Ingbritt (homologous infection) and 6715 (heterologous infection) respectively, 8 days after completion of the initial immunization regimen. Hamsters in experiments 3 and 4 were infected with similar quantities of the heterologous or homologous organisms described above. Prior to this time salivary (and serum) GTF-inhibiting activity could be demonstrated in all the immunized animals. The flora of all animals was periodically monitored by swabbing and plating onto Mitis-Salivarius (MS) agar and MS agar containing 200 μg streptomycin/ml (MSS). Taubman, M. A., and Smith, D. J., *Infect. Immunity* 9.1079, 1974.

At the termination of the experiment saliva was collected and the animals were exsanguinated. Caries and lesions were scored by a modified Keyes method without knowledge of the group designation of the animal, as previously described.

Salivas and sera were collected and treated as previously described. Taubman, M. A. and D. J. Smith, *Infect. Immunity* 9:1079, 1974. In addition, saliva to be used in the inhibition of $^{14}$C-glucose incorporation assays was dialyzed, first against PBS containing 0.02 M EDTA, then against PBS.

EXAMPLE 19

IN VITRO ANTIGENIC RELATEDNESS OF *S. MUTANS* GTF ASSAY FOR INHIBITION OF GTF ACTIVITY

Glucosyltransferase activity was measured by determining the amount of $^{14}$C-glucose incorporation into an ethanol insoluble polysaccharide by glucosyltransferase, first preincubated (1 hour) with sera or saliva, then incubated (2 hours) with $^{14}$C-glucosyl-labelled sucrose and dextran T10 at 37° C. Smith, D. J. and M. A. Taubman, *Infect. Immun.* 15:91, 1977. Inhibition was expressed as the percentage reduction in counts incorporated into precipitated polysaccharide by enzyme in the presence of immune sera (salivas) compared with incorporation by enzyme in the presence of control sera or salivas. The results are tabulated below.

Previous studies, as indicated above, have indicated that antigenic differences exist among GTF synthesized by various serotypes of *S. mutans*. These relationships are further explored herein for serotypes a, c and g by determining the extent to which antisera, prepared by injecting hamsters with GTF eluted from water-insoluble polysaccharide of strains E49, Ingbritt or 6715, would inhibit the formation of polysaccharide by GTF in ammonium-sulfate precipitates of culture supernatants of these three serotypes. Enzyme from serotypes a (E49) and g (6715) are both strongly inhibited by antisera directed to GTF of either serotype, indicating that these two enzyme preparations are antigenically related. Enzyme from serotype c (Ingbritt), while appreciably inhibited by the homologous hamster anti-Ingbritt GTF antisera, is only minimally affected by antisera directed to GTF of serotypes a or g. Conversely, neither the anti-serotype a or g GTF inhibit the Ingbritt enzyme by more than 12%. Based on these inhibition patterns, two subsets of GTF antigens appear to exist within these three serotypes; one subset includes GTF from serotypes a and g while a second subset includes GTF from serotype c. Although enzymes from these two subsets are antigenically distinct on this basis, the inhibition of enzyme by antisera of the heterologous subset, while low, is significant compared with the activity of the enzyme in the presence of sera from sham-immunized hamsters.

| Inhibition of GTF-mediated $^{14}$C-Glucose Incorporation into ETOH-Insoluble Polysaccharide by Hamster Anti-GTF Sera | | | |
|---|---|---|---|
| | Percentage Inhibition of Mean CPM Compared to Normal Sera | | |
| Hamster Sera[a] | E49 GTF | ING GTF | 6715 GTF |
| Anti-E49 GTF | 52 ± 3[b] | 8 ± 1 | 78 ± 3 |
| Anti-ING GTF | 12 ± 3 | 59 ± 2 | 9 ± 4 |
| Anti-6715 GTF | 42 ± 2 | 12 ± 1 | 41 ± 3 |
| Sham-Injected | 0 ± 2 | 2 ± 2 | 0 ± 2 |

[a]Four to 13 sera tested against each enzyme.
[b]Mean ± standard error.

EXAMPLE 20

In Vivo Cross Protection Via Immunization With Serotype c

In order to determine whether the protective effects of GTF immunization could be extended across subset boundaries the following experiment was devised. Hamsters were either sham-immunized with buffer in CFA or immunized with serotype c GTF in CFA earlier set forth. After GTF-inhibitory activity was demonstrated in sera (mean inhibition±SE: 41.2±1.9) and salivas (11.6±3.6) of enzyme-injected groups, hamsters were infected with cariogenic and streptomycin resistant strains of *S. mutans* on day 59. Sham injected group II and Ingbritt GTF-injected group IV were infected with the heterologous serotype g strain 6715. During the course of the 40 day infection period, animals were swabbed 4 days and 21 days after infection to determine the effect of immunization on colonization. The results of these swabbings are presented below. No streptomycin-resistant streptococci were detected in the uninfected group I. The geometric mean of the colony forming units of Ingbritt organisms recovered from GTF-injected group IV were much lower than Ingbritt CFU recovered from the homologously infected, sham-injected group II on days 4 and 21 of infection. These differences were statistically significant on the second occasion. The geometric mean of the colony forming units of 6715 organisms recovered from GTF-injected group V were significantly lower than 6715 CFU recovered from the heterologously infected, sham injected group III on both occasions. Thus, reductions in recoveries of plaque-associated *S. mutans* of both homologous and heterologous serotypes occurred in hamsters immunized with the serotype c GTF.

| *S. Mutans* Colony Forming Units Recovered from Molar Surfaces of Hamsters After Infection With Either *S. Mutans* Serotype c (Groups II and IV) or Serotype g (Groups III and V) | | | |
|---|---|---|---|
| | | Geometric Mean CFU | |
| Group/Treatment/N | Infecting Strain | Day 4[a] (×10$^{-2}$) | Day 21 (×10$^{-3}$) |
| I   Noninfected/6 | None | 0 | 0 |
| II  Sham-immunized/11 | Ingbritt | 33.8 | 238[b] |
| IV  GTF$_{ING}$-immunized/12 | Ingbritt | 9.1 | 17[b] |
| III Sham-immunized/12 | 6715 j | 50.2[c] | 773[d] |
| V   GTF$_{ING}$-immunized/12 | 6715 | 4.6[c] | 43[d] |

[a]Days following infection.
[b,c]Differences between these two groups statistically significant, p < 0.05.
[d]Differences between these two groups statistically significant; p < 0.005.

The effect of local injection with serotype c GTF on the disease caused by Ingbritt and 6715 strains was determined by evaluating the caries and lesions on the molar teeth after the 40 day infection period. The individual immunized hamster caries scores or lesion counts were compared with the mean caries scores or lesion counts of the similarly infected sham-immunized group. These differences are expressed as percentage reductions of sham disease. Both caries scores and lesion counts of GTF-injected hamsters infected with homologous Ingbritt organisms were reduced by at least 60%. The differences in both these parameters between the sham group II and immunized group IV were significant at the 0.001 level. The caries scores and lesions counts of GTF-immunized hamsters infected with strain 6715 (Group V) were at least 50% lower than the mean caries scores and lesions counts in the sham group III infected with the same strain. These differences were significant at the 0.025 and 0.001 level respectively.

A comparison of the percentage reductions in disease of the homologously infected group IV and heterologously infected group V revealed that there was slightly, but not significantly, greater protection observed in homologously infected groups. In either group, reductions in caries scores and lesions counts on smooth surfaces were more prominent than occlusal surface reductions. Thus, the immune response elicited by local injection of serotype c derived GTF interferes with the pathogenesis, especially on smooth surfaces, of these *S. mutans* organisms, regardless of the apparent *in vitro* antigenic unrelatedness of the GTF which they synthesize.

In order to determine whether the protective effects of GTF immunization could be extended across subset boundaries the following experiment was devised. Hamsters were either sham-immunized with buffer in CFA or immunized with serotype c GTF in CFA earlier set forth. After GTF-inhibitory activity was demonstrated in sera (mean inhibition±SE: 53.1±2.5) and salivas 5.2±1.8) of enzyme-injected groups, hamsters were infected with cariogenic and streptomycin resistant strains of *S. mutans* on day 59. Sham injected group II and E49 GTF-injected group IV were infected with the heterologous serotype g strain 6715. During the course of the 40 day infection period, animals were swabbed 4 days and 18 days after infection to determine the effect of immunization on colonization. The results of these swabbings are presented below. No streptomycin-resistant streptococci were detected in the uninfected group I. The geometric mean of the colony forming units of Ingbritt organisms recovered from GTF-injected group IV were significantly lower than E49 CFU recovered from the homologously infected, sham-injected group II on days 4 and 18 of infection. These differences were statistically significant on both occasions.

The geometric mean of the colony forming units of 6715 organisms recovered from GTF-injected group V were significantly lower than 6715 CFU recovered from the heterologously infected, sham injected group III on both occasions. Thus, reductions in recoveries of plaque-associated *S. mutans* of both homologous and heterologous serotypes occurred in hamsters immunized with the serotype a GTF.

*S. mutans* Colony Forming Units Recovered from Molar Surfaces of Hamsters after infection with either *S. mutans* serotype a (Groups II and IV) or serotype g (Groups III and V) (H3)

| Group | Treatment | Infecting strain | N | Geometric Mean CFU Day[a] 4 | Day 18 | Sacrifice Day 46 |
|---|---|---|---|---|---|---|
| I | Non-infected | None | 6 | 0 | Not swabbed | 0 |
| II | Sham-immunized | E49 | 11 | 3090[b] | 446,683[c] | 445 |
| IV | GTF$_{E49}$-immunized | E49 | 11 | 339[b] | 26,303[c] | 103 |
| III | Sham-immunized | 6715 | 11 | 56[d] | 10,964 | 91 |
| V | GTF$_{E49}$-immunized | 6715 | 11 | 8[d] | 589 | 11 |

[a]Days following infection.
[b,c,d]Differences between these two groups statistically significant;
b$_p$<0.001
c$_p$<0.05
d$_p$<0.005

The effect of local injection with serotype c GTF on the disease caused by Ingbritt and 6715 strains was determined by evaluating the caries and lesions on the molar teeth after the 40 day infection period. The individual immunized hamster caries scores or lesion counts were compared with the mean caries scores or lesion counts of the similarly infected sham-immunized group. These differences are expressed as percentage reductions of sham disease. Caries scores of GTF-injected hamsters infected with homologous Ingbritt organisms were reduced by at least 48% and lesion counts by 28%. The differences in these parameters between the sham group II and immunized group IV were significant at the 0.05 level for caries and 0.005 level for lesion. The caries scores counts of GTF-immunized hamsters infected with strain 6715 (Group V) were 42% lower than the mean caries scores in the sham group III infected with the same strain. Lesion counts were 25% lower. The differences in lesions were significant at the 0.05 level.

In Vivo Cross Protection Via Immunization With Serotype c

In order to determine whether the protective effects of GTF immunization could be extended across other subset boundaries the following experiment was devised. Hamsters were either sham-immunized with buffer in CFA or immunized with serotype GTF in CFA earlier set forth. After GTF-inhibitory activity was demonstrated in sera (mean inhibition±SE: 49.0±4.8) and salivas (18±3.5) of enzyme-injected groups, hamsters were infected with cariogenic and streptomycin resistant strains of *S. mutans* on day 59. Sham injected group II and serotype g GTF-injected group IV were infected with the heterologous serotype c strain Ingbritt. During the course of the 54 day infection period, animals were swabbed 14 days and 33 days after infection to determine the effect of immunization on colonization. The results of these swabbings are presented below. No streptomycin-resistant streptococci were detected in the uninfected group I. The geometric mean of the colony forming units of 6715 organisms recovered from GTF-injected group IV were significantly lower than Ingbritt CFU recovered from the homologously infected, sham-injected group II on days 14 and 33 of infection. These differences were statistically significant on both occasions. The geometric mean of the colony forming units of Ingbritt organisms recovered from GTF-injected group V were significantly lower than Ingbritt CFU recovered from the heterologously infected, sham injected group III on both occasions. Thus, reductions in recoveries of plaque-associated *S. mutans* of both homologous and heterologous serotypes occurred in hamsters immunized with the serotype g GTF.

*S. mutans* CFU Recovered by Swabbing (H4)

| Group/Treatment/N | Infecting Strain | Geometric Mean CFU Day 14 ($\times 10^2$) | Day 33 ($\times 10^3$) | At Sacrifice Day 54 ($\times 10^4$) |
|---|---|---|---|---|
| I Noninjected/7 | None | 0 | 0 | 0 |
| II Sham-immunized/12 | 6715 | 504* | 816** | 736 |
| IV GTF$_{6715}$-immunized/12 | 6715 | 87* | 123** | 605 |
| III Sham-immunized/12 | Ingbritt | 556** | 416*** | 516 |

-continued

S. mutans CFU Recovered by Swabbing (H4)

| Group/Treatment/N | Infecting Strain | Geometric Mean CFU Day 14 ($\times 10^2$) | Day 33 ($\times 10^3$) | At Sacrifice Day 54 ($\times 10^4$) |
|---|---|---|---|---|
| V GTF$_{6715}$-immunized/12 | Ingbritt | 33** | 66*** | 372 |

Differences between sham-and GTF-immunized groups statistically significant:
*P < 0.01
**P < 0.001
***P < 0.005

The effect of local injection with serotype c GTF on the disease caused by Ingbritt and 6715 strains was determined by evaluating the caries and lesions on the molar teeth after the 40 day infection period. The individual immunized hamster caries scores or lesion counts were compared with the mean caries scores or lesion counts of the similarly infected sham-immunized group. These differences are expressed as percentage reductions of sham disease. Both caries scores and lesion counts of GTF-injected hamsters infected with homologous Ingbritt organisms were reduced by at least 55%. The differences in caries and lesion these parameters between the sham group II and immunized group IV were significant at the 0.005 and 0.001 levels respectively. The caries scores and lesions counts of GTF-immunized hamsters infected with strain 6715 (Broup V) were at least 56% lower than the mean caries scores and lesions counts in the sham group III infected with the same strain. These differences were significant at the 0.05 and 0.001 level respectively.

The usefulness of a caries vaccine is partly dependent upon the extent to which it demonstrates protection against the serotypes of S. mutans normally associated with human infection. Epidemiologic studies of S. mutans prevalence in human populations have shown that the serotype c strains predominate among those isolated. Serotype d(g) strains have also been isolated fairly frequently. These two groups are not only serologically distinct but also differ with regard to their guanine+cytosine contents, cell wall carbohydrates, antigenic relatedness of their GTF, as shown above, and other biochemical and genetic features. However, despite these differences, local immunization with glucoyltransferase from the serotype c strain elicited a protective immune response against infection with serotype g organisms. Apparently the low but significant level of inhibition noted in the in vitro assay reflected an activity which was protective. This could possibly be explained by the in vivo interference with a critical enzyme function, e.g., insoluble glucan formation, which may not be striking in vitro if our assay favors soluble glucan formation. Antisera directed against enzyme synthesizing insoluble glucan has been reported to be a more effective inhibitor of GTF from different setotypes than antisera directed against GTF synthesizing soluble glucan. Linzer, R. and H. O. Slade, and Kuramitsu, H. and L. Ingersoll, both supra. Since the enzyme antigen in the present study was prepared directly from the insoluble polysaccharide, higher levels of more cross-reactive anti-GTF antibody might be expected to result in enhanced cross-protection.

Previously, primates injected with cell-associated Ingbritt antigens (live, heat-killed or broken cells) showed caries reductions caused by infection with either Ingbritt or a pre-existent serotype c S. mutans flora. Bowen, W. H., Cohen, B., Cole, M. F. and Coleman, G. Brit. Dent. J. 139:45, 1975, Lehner, T., Challacombe, S. J. and Caldwell, J., Archs. Oral Biol. 20:305, 1975. However, those injected with Ingbritt GTF-containing preparations gave little evidence of protection. While this could be explained by a difference in the animal model used for immunization, a more likely explanation may lie in the physical nature and concentration of the GTF used. In our experiments enzyme is eluted from the glucan product with 6 M guanidine-HCl. The elution procedure tends to aggregate the enzyme, rendering it potentially more innumogenic. In addition, the enzyme is derived from water-insoluble polysaccharide which is generally thought to be more significant than the water-soluble form in the pathogenic potential of S. mutans. Gibbons, R. J. and van Houte, J., Ann. Rev. Micro. 29:19, 1975. Furthermore, in contrast to the primate studies, GTF-inhibitory activity was present in sera and salivas of all injected hamsters prior to infection and these levels were maintained by booster injection during the infection period.

The results suggest that the formulation of a caries vaccine may require enzyme antigen from only one strain. However several questions remain, including: (1) whether such cross-protection would occur with GTF from other strains, (2) which specific GTF component elicits the caries-protective antibody response, and (3) by what mechanism does protection occur.

It will be understood that various changes may be made in the preferred embodiments described hereinabove without departing from the scope of the present invention. Accordingly, the preceding should be construed as illustrative and not in a limiting sense.

What is claimed is:

1. In a method of recovering glucosyltransferase (GTF) for use in immunization against dental caries, which method comprises:
   (a) culturing Streptococcus mutans in a medium containing glucose and essentially dialyzable nutrients to form a mixture of culture cells and supernatant;
   (b) removing the cells for the culture supernatant;
   (c) incubating the recovered supernatant with a polysaccharide to synthesize water-insoluble polysaccharide;
   (d) recovering the water-insoluble polysaccharide;
   (e) washing the polysaccharide to remove water-soluble contaminants; and
   (f) recovering the GTF from the water-insoluble polysaccharide, the improvement which comprises
   (i) incubating the washed water-insoluble polysaccharide from the supernatant with a denaturing solvent to break the bond between the water-insoluble polysaccharide and the GTF enzyme,
   (ii) separating the water-insoluble polysaccharide from the denaturing solvent containing the GTF enzyme,
   (iii) separating the denaturing solvent from the GTF in the supernatant, and
   (iv) concentrating the GTF enzyme to provide a concentrated GTF consisting of essentially purified GTF suitable for use for preventing dental caries.

2. The method of claim 1 which comprises employing as the Streptococcus mutans a Streptococcus mutans selected from the group consisting of strain 6715, strain Ingbritt or strain E49.

3. The method of claim 1 wherein the culture medium is brain heart infusion containing about 1% glucose and which includes culturing the culture medium for about 20 hours at 37° C.

4. The method of claim 1 which includes incubating the culture supernatant with about 10% sucrose for about 48 hours at 37° C. and at a pH of about 6.5.

5. The method of claim 1 wherein the denaturing solvent is selected from the group consisting of quanidine-HCl, urea and dodecylsulfate.

6. The method of claim 1 which includes concentrating the GTF enzyme by gel filtration, and wherein the GTF is eluted on phenyl-sepharose in about 6 M quanidine-HCl as the denaturing solvent.

7. The method of claim 1 which includes employing a saline concentration of from about one to two times of the denaturing solvent with the water-insoluble polysaccharide.

8. The method of claim 1 which includes incubating the recovered supernatant with sucrose.

9. The method of claim 1 which includes concentrating the GTF enzyme by gel filtration.

10. The method of claim 1 wherein the denaturing solvent is guanidine-HCl and which includes removing the denaturing solvent from the supernatant by dialysis.

11. The method of claim 1 which includes concentrating a purified GTF enzyme to a specific activity of 2.7 and a GTF/FTF of greater than about 97%.

12. The method of claim 1 which includes preparing a vaccine for preventing dental caries wherein the concentrated GTF comprises the active ingredients of the vaccine.

13. In a method of recovering glucosyltransferase (GTF) for use in a vaccine for immunization against dental caries, which method comprises:
  (a) culturing *Streptococcus mutans,* selected from the group consisting of strain 6715, strain Ingbritt or strain E49, in a medium containing glucose and essentially dialyzable nutrients to form a mixture of culture cells and supernatant;
  (b) removing the cells for the culture supernatant;
  (c) incubating the recovered supernatant with sucrose to synthesize water-insoluble polysaccharide;
  (d) recovering the water-insoluble polysaccharide;
  (e) washing the polysaccharide to remove water-soluble contaminants; and
  (f) recovering the GTF from the water-insoluble polysaccharide,
the improvement which comprises
  (i) incubating the washed water-insoluble polysaccharide from the supernatant with a guanidine-HCl denaturing solvent to break the bond between the water-insoluble polysaccharide and the GTF enzyme,
  (ii) separating the water-insoluble polysaccharide from the denaturing solvent containing the GTF enzyme,
  (iii) separating the denaturing solvent from the GTF in the supernatant, and
  (iv) concentrating the GTF enzyme by gel filtration to provide an eluent consisting of essentially purified GTF suitable for use in vaccine form for preventing dental caries.

* * * * *